United States Patent [19]

Ashton et al.

[11] Patent Number: 4,617,304

[45] Date of Patent: Oct. 14, 1986

[54] PURINE DERIVATIVES

[75] Inventors: Wallace Ashton, Clark, N.J.; Edward Walton, Sun City West, Ariz.; Richard L. Tolman, Warren, N.J.

[73] Assignee: Merck & Co., Inc., Rahway, N.J.

[21] Appl. No.: 598,612

[22] Filed: Apr. 10, 1984

[51] Int. Cl.$^4$ .................... C07D 473/18; A61K 31/52
[52] U.S. Cl. .................................... 514/261; 514/262; 544/276; 544/277; 544/320
[58] Field of Search ................ 544/277, 276; 424/253; 514/261, 262

[56] References Cited

U.S. PATENT DOCUMENTS 4,230,708 10/1980 DeClercq et al. ................... 424/253
4,294,831 10/1981 Schaeffer ............................ 544/277

OTHER PUBLICATIONS

Pandit, et al., Synthetic Communications, 2(6), 345–351 (1972).

Primary Examiner—Nicholas S. Rizzo
Attorney, Agent, or Firm—Richard A. Elder; Hesna J. Pfeiffer

[57] ABSTRACT

Purines and pyrimidines having a fused cyclopropane ring in the side chain and the heterocyclic isosteres of said purines and pyrimidines have antiviral activity, especially against viruses of the herpes class.

8 Claims, No Drawings

PURINE DERIVATIVES

BACKGROUND OF THE INVENTION

The present invention relates to hydroxyalkyl substituted purines and pyrimidines having a fused cyclopropane ring in the hydroxyalkyl side chain and the heterocyclic isosteres of said purines and pyrimidines. These compounds have antiviral activity. The compounds are particularly effective against herpes viruses, e.g. herpes simplex virus. The present invention also relates to processes for preparing such compounds.

The compounds of the invention may be represented by the formula

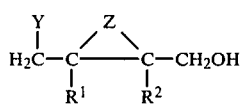

and the pharmaceutically acceptable salts thereof wherein Y is a purin-9-yl or a pyrimidin-1-yl or a heterocyclic isostere of a purin-9-yl or a pyrimidin-1-yl group; $R^1$ is selected from hydrogen and alkyl of 1 to 4 carbon atoms; $R^2$ is selected from hydrogen, alkyl of 1 to 4 carbon atoms and —CH$_2$OH; and Z is >CH$_2$ or >O.

Preferably, Y is guanine, a guanine isostere, adenine, cytosine, uracil, thymine or 2-amino-6-chloropurine.

Most preferably, Y is guanine.

An isostere is a molecule which is isosteric with another molecule; that is, has a similarity of structure and a resulting similarity of properties exhibited by the molecules. The molecules may contain different atoms and not necessarily the same number of atoms, but possess the same total or valence elections in the same arrangement, viz. carbon monoxide (C=O) and atmospheric nitrogen (N=N), or cyanide ion (—C≡N) and acetylide ion (—C≡CH).

Other heterocyclic systems isosteric with purine include 7-deazapurine (e.g. pyrrolo[2,3-d]pyrimidine), 8-azapurine (e.q. v-triazolo[4,5-d]pyrimidine), 3-deazapurine (e.g. imidazo[4,5-C]pyridine), and 1-deaza-5-azapurine (e.g. s-triazolo-[2,3-a]pyrimidine etc. Some heterocyclic systems isosteric with oxopyrimidines include 3-deazauracil (e.g. 2,4-dihydroxypyridine), 6-azauracil (e.g. 3,5-dihydroxy-1,2,4-triazine), and 5-azacytosine (2-amino-4-hydroxy-1,3,5-triazine).

The following are representative compounds of the present invention:
9-[(E)-2-(Hydroxymethyl)cyclopropylmethyl]guanine
9-[(Z)-2-(Hydroxymethyl)cyclopropylmethyl]guanine
9-[(E)-2-(Hydroxymethyl)cyclopropylmethyl]adenine
9-[(Z)-2-(Hydroxymethyl)cyclopropylmethyl]adenine
9-[2,2-Bis(hydroxymethyl)cyclopropylmethyl]guanine
9-[2,2-Bis(hydroxymethyl)cyclopropylmethyl]adenine
9-[(E)-2,3-Epoxy-4-hydroxybutyl]guanine
9-[(Z)-2,3-Epoxy-4-hydroxybutyl]guanine
9-[(E)-2,3-Epoxy-4-hydroxybutyl]adenine
9-[(Z)-2,3-Epoxy-4-hydroxybutyl]adenine
9-[(E)-2-Hydroxymethyl-1,2-dimethylcyclopropylmethyl]guanine
9-[(Z)-2-Hydroxymethyl-1,2-dimethylcyclopropylmethyl]guanine
9-[(E)-2-Hydroxymethyl-1,2-dimethylcyclopropylmethyl]adenine
9-[(Z)-2-Hydroxymethyl-1,2-dimethylcyclopropylmethyl]adenine
9-[(E)-2-(Hydroxymethyl)cyclopropylmethyl]-2-amino-6-chloropurine
9-[(Z)-2-(Hydroxymethyl)cyclopropylmethyl]-2-amino-6-chloropurine
9-[2,2-Bis(hydroxymethyl)cyclopropylmethyl]-2-amino-6-chloropurine
9-[(E)-2,3-Epoxy-4-hydroxybutyl]-2-amino-6-chloropurine
9-[(Z)-2,3-Epoxy-4-hydroxybutyl]-2-amino-6-chloropurine
9-[(E)-2-Hydroxymethyl-1,2-dimethylcyclopropylmethyl]-2-amino-6-chloropurine
9-[(Z)-2-Hydroxymethyl-1,2-dimethylcyclopropylmethyl]-2-amino-6-chloropurine
1-[(E)-2-(Hydroxymethyl)cyclopropylmethyl]thymine
1-[(Z)-2-(Hydroxymethyl)cyclopropylmethyl]thymine
1-[(E)-2-(Hydroxymethyl)cyclopropylmethyl]uracil
1-[(Z)-2-(Hydroxymethyl)cyclopropylmethyl]uracil
1-[2,2-Bis(hydroxymethyl)cyclopropylmethyl]thymine
1-[2,2-Bis(hydroxymethyl)cyclopropylmethyl]uracil
1-[(E)-2,3-Epoxy-4-hydroxybutyl]thymine
1-[(Z)-2,3-Epoxy-4-hydroxybutyl]thymine
1-[(E)-2,3-Epoxy-4-hydroxybutyl]uracil
1-[(Z)-2,3-Epoxy-4-hydroxybutyl]uracil
1-[(E)-2-Hydroxymethyl-1,2-dimethylcyclopropylmethyl]thymine
1-[(Z)-2-Hydroxymethyl-1,2-dimethylcyclopropylmethyl]thymine
1-[(E)-2-Hydroxymethyl-1,2-dimethylcyclopropylmethyl]uracil
1-[(Z)-2-Hydroxymethyl-1,2-dimethylcyclopropylmethyl]uracil
1-[(E)-2-(Hydroxymethyl)cyclopropylmethyl]cytosine
1-[(Z)-2-(Hydroxymethyl)cyclopropylmethyl]cytosine
1-[(2,2)-Bis(hydroxymethyl)cyclopropylmethyl]cytosine
1-[(E)-2,3-Epoxy-4-hydroxybutyl]cytosine
1-[(Z)-2,3-Epoxy-4-hydroxybutyl]cytosine
1-[(E)-2-Hydroxymethyl-1,2-dimethylcyclopropylmethyl]cytosine
1-[(Z)-2-Hydroxymethyl-1,2-dimethylcyclopropylmethyl]cytosine.

The following compounds are preferred:
9-[(Z)-2-(Hydroxymethyl)cyclopropylmethyl]guanine
9-[(Z)-2-(Hydroxymethyl)cyclopropylmethyl]adenine
9-[2,2-Bis(hydroxymethyl)cyclopropylmethyl]adenine
9-[2,2-Bis(hydroxymethyl)cyclopropylmethyl]guanine.

The compounds of the present invention may be prepared by various methods. The following three schemes illustrate these methods:

Scheme I

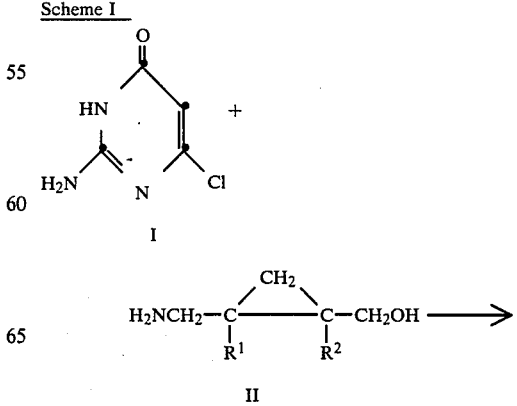

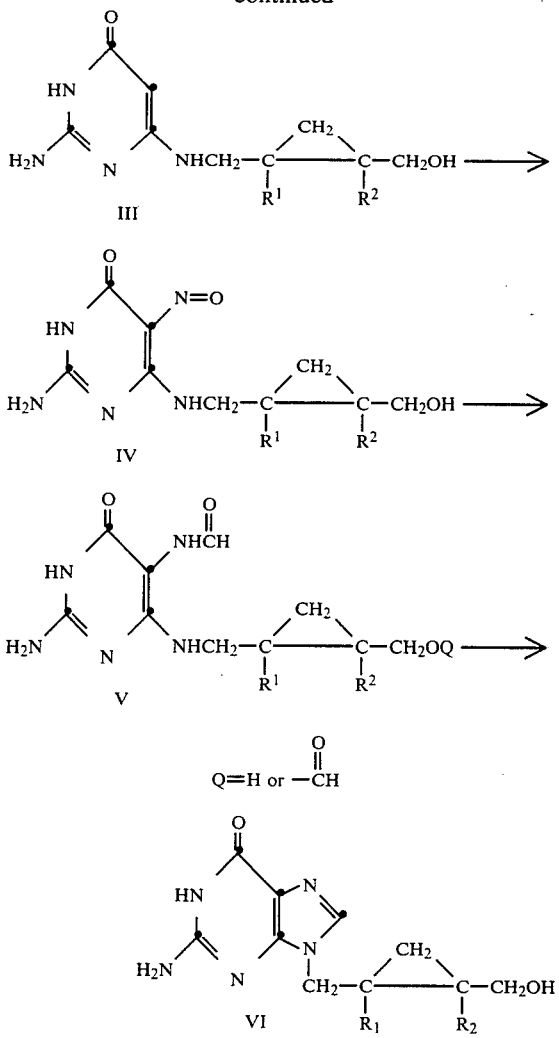

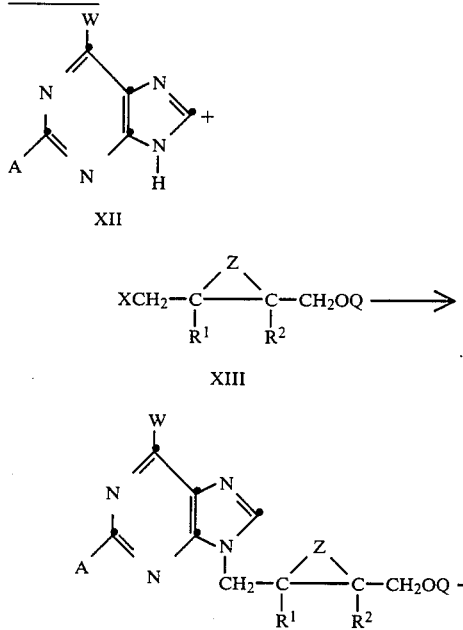

Scheme II

Scheme III

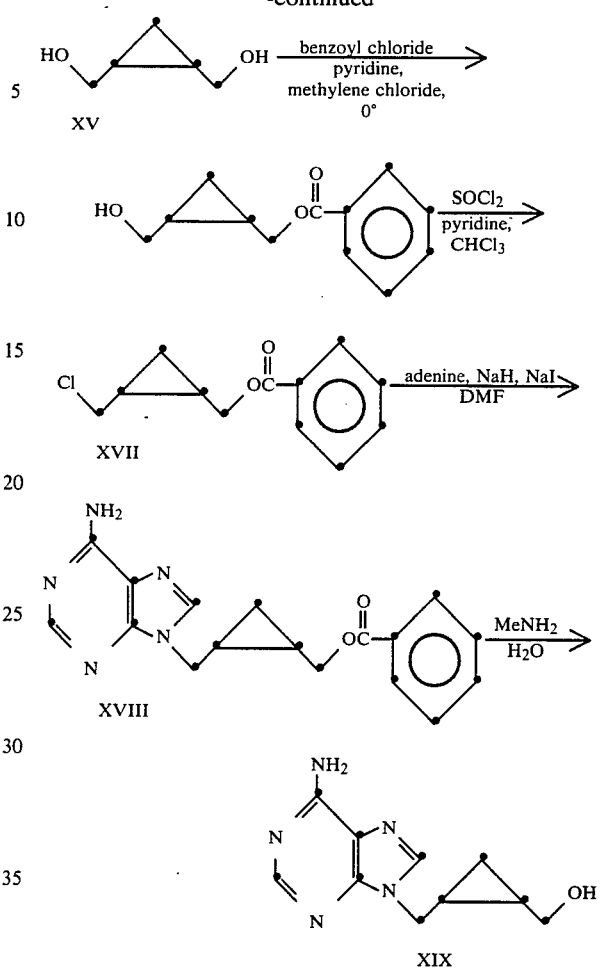

According to one method (Scheme I), which is similar to that of Noell et al., *J. Med. Pharm. Chem.*, 5, 558 (1962), 6-chloroisocytosine of Formula I, [2-amino-6-chloro-4(3H)-pyrimidinone]is reacted with an excess amount of the appropriate amino alcohol of Formula II. The reaction is conducted at elevated temperature in a suitable high boiling, polar solvent, preferably 2-ethoxyethanol, at reflux. Preferably, about three equivalents of the compound of Formula II are used per equivalent of the compound of Formula I. Alternatively, a lesser amount of the compound of Formula II, preferably from about 1.5 to 2 equivalents, may be used if a compatible base is added to the reaction mixture to scavenge the HCl liberated during the reaction. Compatible bases include high-boiling tertiary aliphatic amines such as 1,4-diazabicyclo[2.2.2]-octane (DABCO). The reaction is run for from about 1 to about 18 hours, preferably for from about 1 to about 3 hours.

The resulting 6-(hydroxyalkylamino)isocytosine of Formula III need not be isolated but may be treated directly with sodium nitrite in aqueous acetic acid at about room temperature to give the 5-nitroso derivative of Formula IV which is readily isolated. Reduction of the nitroso group of the compound of formula IV gives the compound of formula V. The nitroso group of the compound of Formula IV is reduced under conditions such that the resulting amino group is formylated in situ (at least partial formylation of the terminal hydroxyl group of the side chain also normally occurs under these conditions). The reduction and formylation may be carried out by a variety of methods such as, for example, sodium dithionite in the presence of formic acid, or zinc dust in formic acid, or catalytic hydrogenation (e.g., using 10% palladium on carbon) in formic acid. The compound of Formula V is usually reacted directly in the next step without purification. Cyclization of the 5-formamido-6-(substituted-alkylamino)isocytosine to a guanine derivative may be accomplished by various means such as, for example, heating with formamide in the presence of formic acid at elevated temperature of from 150° to about 190° (bath temperature) for from about 2 to about 4 hours or by other methods described in the literature, for example, Lister, "Fused Pyrimidines, Part II: Purines", editor, D. J. Brown, John Wiley and Sons, Inc., 1971, Chapter II. Final treatment with a warm aqueous base such as, e.g., methylamine or sodium hydroxide solution, serves to remove any residual formyl groups and allows the isolation of the compound of Formula VI.

Similarly, isosteres of compounds of Formula VI may be prepared from intermediates having the Formula III or IV. For example, cyclization of III with chloroacetaldehyde in sodium acetate buffer and deprotection produces the corresponding 7-deazapurine analogue of the compound of Formula VI. Similarly, chemical or catalytic reduction of IV produces the 5-amino derivative which may be cyclized to the 8-azapurine isostere of the compound of Formula VI after appropriate deprotection. Thus, an important embodiment of the invention relates to compounds of the Formulae III, IV and V and the 5-amino analogues thereof.

The 9-substituted guanines of Formula VI may also be prepared (Scheme II) by alkylation of a preformed purine derivative of Formula XII (e.g., 2,6-dichloropurine, 2-amino-6-chloropurine or 2-amino-6-benzyloxypurine) with a compound of Formula XIII, wherein X is a leaving group such as bromo, chloro, iodo, tosyl, mesyl and the like, and Q is a protecting group removable by hydrolysis such as, for example, benzoyl or acetyl, or by hydrogenolysis such as, for example, benzyl. The alkylation is normally carried out in the presence of a base such as, for example, potassium carbonate, in a suitable solvent such as, for example, dimethylformamide or dimethylsulfoxide. The 9-alkylated product of Formula XIV may be separated from any isomers (e.g., the 7-alkylated isomer) chromatographically or by other means. Transformation of the substituents Z and W to give the guanine and removal of the protecting group Q may be accomplished by standard methods known to those skilled in the art.

Scheme III illustrates the preparation of 9-[(Z)-2-(hydroxymethyl)cyclopropylmethyl]adenine. The chloromethylcyclopropane XVII may also be used to alkylate other purines (e.g. 6-chloropurine, which may be converted to an adenine using known methods, or 2,6-dichloropurine or 2-amino-6-chloropurine, which may be converted to a guanine using known methods) or to alkylate pyrimidines or other isosteric heterocyclic systems. The following schemes IV and V illustrate alkylation of pyrimidines:

Scheme IV

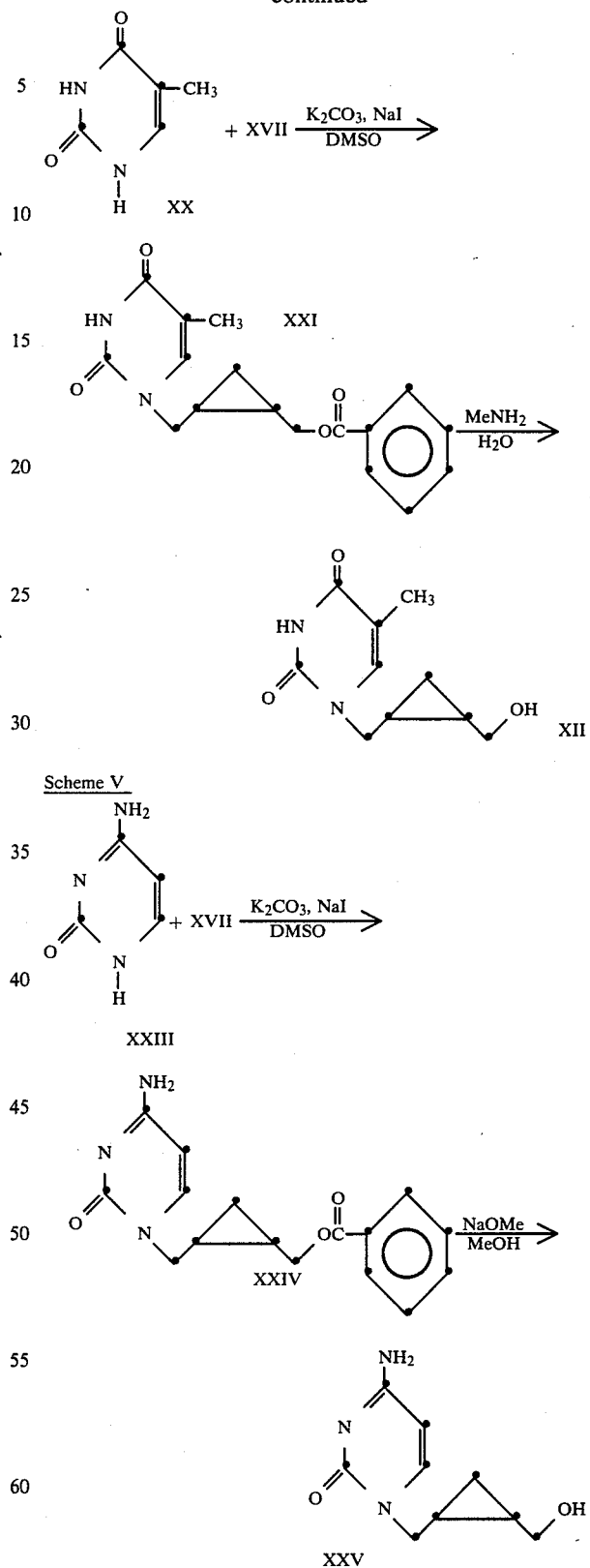

Scheme V

The pyrimidines, thymine (XX) and cytosine (XXIII) are reacted with the chloromethylcyclopropane XVII (Schemes IV and V, respectively) in the presence of sodium iodide and a base such as potassium carbonate in a polar solvent such as dimethyl sulfoxide or dimethyl formamide, preferably at a temperature of about 70 to 90° C. The alkylated pyrimidines may be purified by chromatography. The benzoyl protecting group may then be removed by standard conditions such as aqueous methylamine, methanolic ammonia, or catalytic sodium methoxide in methanol.

The synthetic schemes II–V are readily amenable to the synthesis of isosteric purine and oxypyrimidine compounds. This may be accomplished by simply substituting the appropriately preformed isosteric heterocycle for the purine or oxypyrimidine which undergoes the alkylation reaction, i.e., Compound XII in Scheme II; adenine in Step 3, Scheme III; Compound XX in Scheme IV; and Compound XXIII in Scheme V.

Pharmaceutically acceptable salts are prepared by recrystallization of the desired adenine guanine, 2-amino-6-chloropurine, cytosine, uracil or thymine derivative as the free base or as the acetate or hydrochloride from the aqueous dilute acid of choice. Acid addition salts of adenine derivatives are more stable than the corresponding salts of guanine derivatives. Alkali metal salts of guanine, thymine and uracil derivatives can be made by standard techniques, for example, by dissolving such derivative in water containing one equivalent of an alkali metal hydroxide, followed by evaporation to dryness.

In another aspect of the invention there is provided a pharmaceutical composition or preparation comprising a compound of the formula

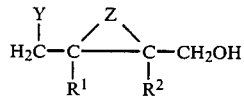

wherein Y, Z, $R^1$ and $R^2$ are as hereinbefore defined; or a pharmaceutically acceptable salt thereof, together with a pharmaceutically acceptable carrier therefor. In a particular aspect the pharmaceutical composition comprises a compound of the present invention in effective unit dosage form.

As used herein the term "effective unit dosage" or "effective unit dose" is denoted to mean a predetermined antiviral amount sufficient to be effective against the viral organisms in vivo. Pharmaceutically acceptable carriers are materials useful for the purpose of administering the medicament, and may be solid, liquid or gaseous materials, which are otherwise inert and medically acceptable and are compatible with the active ingredients.

These pharmaceutical compositions may be given parenterally, orally, used as a suppository or pessary, applied topically as an ointment, cream, aerosol, powder, or given as eye or nose drops, etc., depending on whether the preparation is used to treat internal or external viral infections.

For internal infections the compositions are administered orally or parenterally at dose levels of about 0.1 to 250 mg per kg, preferably 1.0 to 50 mg per kg of mammal body weight, and are used in man in a unit dosage form, administered, e.g. a few times daily, in the amount of 1 to 250 mg per unit dose.

For oral administration, fine powders or granules may contain diluting, dispersing and/or surface active agents, and may be presented in a draught, in water or in a syrup; in capsules or sachets in the dry state or in a non-aqueous solution or suspension, wherein suspending agents may be included; in tablets, wherein binders and lubricants may be included; or in a suspension in water or a syrup. Where desirable or necessary, flavoring, preserving, suspending, thickening or emulsifying agents may be included. Tablets and granules are preferred, and these may be coated.

For parenteral administration or for administration as drops, as for eye infections, the compounds may be presented in aqueous solution in a concentration of from about 0.1 to 10%, more preferably 0.1 to 7%, most preferably 0.2% w/v. The solution may contain antioxidants, buffers, etc.

Alternatively, for infections of the eye, or other external tissues, e.g. mouth and skin, the compositions are preferably applied to the infected part of the body of the patient as a topical ointment or cream. The compounds may be presented in an ointment, for instance, with a water soluble ointment base, or in a cream, for instance with an oil in water cream base, in a concentration of from about 0.1 to 10%, preferably 0.1 to 7%, most preferably 1% w/v.

The following examples illustrate the present invention without, however, limiting the same thereto. All temperatures are expressed in degrees Celsius.

EXAMPLE 1

(Z) and (E)-9-[2-(Hydroxymethyl) cyclopropylmethyl]guanine

Step A-1: Ethyl trans- and cis-2-cyanocyclopropanecarboxylate ((E) and (Z) respectively)

These materials were prepared essentially according to the procedure of V. I. Ivanskii and V. N. Maksimov, J. Org. Chem. U.S.S.R., 8, 54 (1972). Acrylonitrile (38 g.) was stirred under reflux in an oil bath as ethyl diazoacetate (40 g.) was added portionwise over a period of 2.5 hours. After completion of the addition, the mixture was stirred at reflux for an additional 1.5 hours. The excess acrylonitrile was then removed by distillation. The temperature was raised to 125°–130° and maintained there until nitrogen evolution ceased (about 2 hours). Finally, the mixture was heated at 160°–170° for 0.5 hours. After cooling to room temperature overnight under nitrogen, the material was distilled in vacuo. Two major fractions were collected. Fraction 1 was collected at 95°–100° (4.75 mm) and amounted to 17.2 g. of colorless liquid. Fraction 2 was collected at 110°–122° (4.75 mm) and then at 80°–90° (0.5 mm). After filtering to remove a white solid contaminant, fraction 2 amounted to 12 g. Whereas fraction 1 was homogeneous by TLC (1:1 hexane-ethyl acetate), fraction 2 was impure. Fraction 2 was thus subjected to preparative HPLC (silica gel, 7:3 hexane-ethyl acetate, refractive index detection, 3 cycles). Chromatographic fractions containing clean product (lower Rf than fraction 1 on silica gel TLC) were combined and concentrated in vacuo to give 8.53 g of colorless liquid. NMR studies, including proton decoupled $^{13}C$ NMR confirmed that the lower-boiling product (distillation fraction 1) was the trans-isomer, while the higher-boiling product (purified material from distillation fraction 2) was the cis-isomer. Ivanskii and Maksimov reported a boiling point of 82°–83° (5 mm) for the trans-isomer and did not report isolation of the cis-isomer. R. D. Allan, D. R. Curtis, P. M. Headley, G. A. R. Johnston, D. Lodge, and B. Twitchin, J. Neurochem., 34, 652 (1980) obtained both the trans- and cis- isomers by this method and separated them by fractional distillation, but no boiling points or other physical properties were given.

The following is an alternative synthesis of the cis-isomer ((Z)):

Step A-2: Ethyl (Z)-2-cyanocyclopropanecarboxylate

This material was prepared essentially according to the method of V. I. Ivanskii, I. A. D'yakonov, and T. M. Gundalova, *J. Org. Chem. U.S.S.R.*, 3, 1302 (1967) and L. L. McCoy, *J. Org. Chem.*, 25, 2078 (1960). A suspension of 8.4 g. (200 mmole) of sodium hydride (57% in oil) in 40 ml of toluene was stirred mechanically under a nitrogen blanket with intermittent cooling in an ice bath to maintain an internal temperature of 15°–20°. To this was added dropwise, over a period of 20 minutes, a mixture of 10.6 g. (20 mmole) of acrylonitrile and 24.5 g. (200 mmole) of ethyl chloroacetate. After about 1 hour at room temperature, the reaction mixture was warmed to 45°–55°. After 1 hour at this temperature, 1.0 ml of methanol was added dropwise, resulting in vigorous gas evolution, darkening, and a slight exotherm. After an additional 3 hours, 10.2 ml of absolute ethanol was added dropwise, leading initially to vigorous foaming and a brief exotherm to about 70°. After cooling and stirring overnight at room temperature, the mixture was partitioned between ethyl acetate and $H_2O$. The ethyl acetate fraction was washed further with $H_2O$, then dried over magnesium sulfate, treated with charcoal, and filtered through Super-Cel. Concentration of the filtrate gave a residual oil consisting of two liquid phases. This material was further partitioned between methanol and pentane to remove mineral oil. Evaporation of the methanol fraction gave 10.8 g, of orange-brown oil, which was vacuum-distilled through a Vigreux column. The purest material (1.71 g of colorless liquid) was collected at 85°–88° (0.7 mm), although additional material of somewhat lesser purity was collected at 77°–85° (0.7 mm) (1.87 g) and at greater than 94° (0.7 mm) (0.54 g.). The material was identical by NMR, IR, and TLC (thin layer chromatography) to the higher-boiling product (identified as the cis-isomer) from the reaction of acrylonitrile with ethyl diazoacetate. This result casts doubt on the suggestion by Ivanskii, D'yakonov, and Gundalova that the ethyl 2-cyanocyclopropanecarboxylate obtained from the base-induced reaction of acrylonitrile with ethyl chloroacetate may be the trans-isomer. The result is consistent, however, with McCoy's observations that the cis-isomer normally predominates in this type of reaction.

Step B-1: (Z)-2-(Aminomethyl)cyclopropanemethanol

A mixture of 3.42 g (90 mmole) of lithium aluminum hydride and 100 ml of dry tetrahydrofuran was stirred at gentle reflux under nitrogen as a solution of 8.35 g (60 mmole) of ethyl (Z)-2-cyanocyclopropanecarboxylate in 20 ml of tetrahydrofuran was introduced dropwise over a period of about 2 hours. After an additional 2 hours, the reaction was cooled. The mixture was stirred in an ice bath and maintained under nitrogen as 20 ml of water was added dropwise with caution at such a rate that the temperature remained below 20°. During the first part of the addition, there was vigorous gas evolution, followed by heavy precipitation. After stirring for several minutes, the precipitated solid was removed by filtration and washed with tetrahydrofuran. The combined filtrate and washings were dried over sodium sulfate, then filtered, and concentrated by rotary evaporation. The residual oil was distilled through a short-path apparatus to give 3.67 g (60%) of colorless liquid, bp 51-58° (0.2 mm). A boiling point of 55°–58° (0.1 mm) was reported for this compound by J. G. Cannon, A. B. Rege, T. L. Gruen, and J. P. Long, *J. Med. Chem.*, 15, 71 (1972). The material showed satisfactory purity by TLC (70:30:3 chloroform-methanol-concentrated ammonium hydroxide), and the structure was confirmed by NMR.

Step B-2: (E)-2-(Aminomethyl)cyclopropanemethanol

This compound, prepared analogously to the (Z)-isomer, was obtained in 53% yield as a pale yellow, somewhat viscous oil, bp 79°–82° (1.2–1.4 mm). A boiling point of 51° (0.5 mm) was reported for this compound by J. G. Cannon, A. B. Rege, T. L. Gruen, and J. P. Long, *J. Med. Chem.*, 15, 71 (1972). The material showed satisfactory purity by TLC (70:30:3 chloroform-methanol-concentrated ammonium hydroxide), and the structure was confirmed by NMR.

Step C-1:
6-[(Z)-2-(Hydroxymethyl)cyclopropylmethylamino]-5-nitrosoisocytosine

A solution of 3.28 g (20 mmole) of 6-chloroisocytosine monohydrate, 3.54 g (35 mmole) of (Z)-2-(aminomethyl)cyclopropanemethanol, and 1.12 g (10 mmole) of 1,4-diazabicyclo[2.2.2]octane in 9 ml of 2-ethoxyethanol was stirred at reflux under nitrogen. After 2.5 hours the solution was cooled and concentrated on a rotary evaporator under high vacuum. The residual gum was dissolved with heating in 15 ml of glacial acetic acid, then diluted with 10 ml of water, and cooled in ice. The solution was then stirred at ambient temperature as a solution of 2.76 g (40 mmole) of sodium nitrite in 15 ml of water was added. The resulting solution immediately turned dark, followed rapidly by thick precipitation and foaming. The foaming gradually subsided. After about 2 hours, the precipitated solid was collected on a filter and washed thoroughly with water, then with acetone, to give 1.28 g of orange powder, mp 228.5°–229° dec. TLC (80:20:2 chloroform-methanol-water) showed a trace of impurity at the origin. An analytical sample (light orange crystals, mp 234°–235° dec.) was obtained by recrystallization from water. The structure was confirmed by NMR.

Analysis Calculated for $C_9H_{13}N_5O_3$: C, 45.18; H, 5.48; N, 29.28. Found: C, 45.35; H, 5.61; N, 29.26.

Step C-2:
6-[(E)-2-(Hydroxymethyl)cyclopropylmethylamino]-5-nitrosoisocytosine

This compound, prepared analogously to the (Z)-isomer, was obtained as orange-tan crystals, mp 227°–228° dec. The material showed satisfactory purity by TLC (80:20:2 chloroform-methanol-water), and the structure was verified by NMR.

Analysis Calculated for $C_9H_{13}N_5O_3.H_2O$: C, 42.02; H, 5.88; N, 27.23. Found: C, 42.15; H, 5.57; N, 27.26.

Step D-1:
9-[(Z)-2-[2-(Hydroxymethyl)cyclopropylmethyl]guanine

A mixture of 717 mg (3 mmole) of 6-[(Z)-2-hydroxymethyl)cyclopropylmethylamino]-5-nitrosoisocytosine, 50 mg of 10% palladium on carbon, and 10 ml of 88% formic acid was shaken with hydrogen at an initial pressure of 48 psig. Uptake of hydrogen was complete within 30 minutes. The catalyst was removed by filtration, and the filtrate was concentrated on a rotary evaporator under high vacuum. The residual gum was dissolved with heating in 3 ml of formamide and treated with 0.3 ml of 95–97% formic acid. The solution was stirred under nitrogen in an oil bath at approximately 170°. After 2 hours, the solution was cooled and concentrated under high vacuum. The residual semi-solid was extracted with methanol, and the insoluble solid was removed by filtration. Evaporation of the filtrate gave a residual oil, which was dissolved in about 2 ml of 40% methylamine (aqueous). This solution was heated on a steam bath for a few minutes, then diluted with 10 ml of water, treated with charcoal, and filtered through Super-Cel. The filtrate was concentrated by rotary evaporation and dried under high vacuum. The residual oil crystallized on trituration with a little water. Recrystallization from a small volume of water yielded 124 mg of golden crystals. The bulk of this material was recrystallized two more times from water, giving 32 mg of light yellow crystals, mp 311°–314° dec. The material showed satisfactory purity by TLC (80:20:2 chloroform-methanol-water), and the structure was confirmed by 300 MHz NMR.

Analysis Calculated for $C_{10}H_{13}N_5O_2 \cdot 0.33H_2O$: C, 49.78; H, 5.71; N, 29.03. Found: C, 49.75; H, 5.85; N, 29.06.

Step D-2:
9-[(E)-2-Hydroxymethyl)cyclopropylmethyl]]guanine

By a procedure analogous to that used for the (Z)-isomer, this compound was obtained as small, cream-colored plates, mp 273°–275°. The material showed satisfactory purity by TLC (80:20:2 chloroform-methanol-water), and the structure was confirmed by NMR.

EXAMPLE 2

9-[2,2-Bis(hydroxymethyl)cyclopropylmethyl]guanine

Step A: 1,1-Bis(hydroxymethyl)-2-vinylcyclopropane

A solution of 23 g (0.108 mole) of diethyl 2-vinylcyclopropane-1,1-dicarboxylate in 90 ml of dry THF (tetrahydrofuran) was added dropwise to 196 ml of 1M LAH (lithium aluminum hydride) which was stirred and heated at 68°. The addition required 30 minutes and heating and stirring were continued for 2 hours. TLC in cyclohexane-ethyl acetate (1:1) and CHCl$_3$ MeOH (9:1) showed that the reaction was complete. The reaction was cooled to 0° and a total of 200 ml of water was continuously added. After being stirred for 15 minutes, the mixture was filtered and the solid was washed with THF. The combined filtrates were concentrated to yield 12.9 g (93%) of the title compound, $R_f$ CHCl$_3$-MeOH (9:1) 0.45.

NMR (CDCl$_3$): 5.89 (oct, 1H, J=8, 10, 16.5 Hz), 5.36 (oct, 1H, J=16.5, 2, 0.8 Hz), 5.24 (oct 1H, J=10, 2, 0.6 Hz), 3.98, 3.74 (q, 2H; J=14 Hz), 3.74 (s, 2H), 1.58–1.70 (m, 1H), 0.88 (dd, 1H, J=8.5 and 5.5 Hz), 0.69 (tr, 1H, J=5.5 Hz).

Step B:
1,1-Bis(benzoyloxymethyl)-2-vinylcyclopropane

A solution of 5.5 g (43 mmoles) of 1,1-bis(hydroxymethyl)-2-vinylcyclopropane in 40 ml of pyridine was cooled to 0° and 18.5 g (130 mmoles; 15.2 ml) of benzoyl chloride was added dropwise over 15 minutes. The mixture was stirred at 22° for 2 hours. TLC in cyclohexane-EtOAc (4:1) indicated that the reaction was complete. The reaction mixture was treated with 8 ml of water and stirred at 22° for 20 hours. It was concentrated to a residual oil and redissolved in 150 ml of EtOAc and washed with 50 ml of water, three 50-ml portions of 2N HCl, four 50 ml portions of saturated NaHCO$_3$, dried (MgSO$_4$), filtered and concentrated to give 11 g (75%) of the title compound, R$_f$ cyclohexane-ethyl acetate (4:1) 0.7.

NMR (CDCl$_3$) δ: 7.36–8.04 (m, 10 H), 5.78 (oct 1H, J=17, 10, 7.5 Hz), 5.24 (oct 1H, J=17, 1.7, 1 Hz), 5.51 (oct 1H, J=10, 1.6, 0.8), 4.29, 4.65 (q, 2H, J=12 Hz), 4.13, 4.23 (q, 2H, J=11.5 Hz), 2.80–2.92 (m, 1H) 1.12, 1.17 (dd, 1H, J=8.5, 5.5 Hz), 0.98 (Tr, 1H, J=5.5 Hz).

Step C:
1,1-Bis(benzoyloxymethyl)-2-hydroxymethylcyclopropane

A solution of 11 g (33 mmoles) of 1,1-bis(benzoyloxymethyl)-2-vinylcyclopropane in 200 ml of CH$_2$Cl$_2$ was cooled to −70° and stirred while a stream of O$_3$ was introduced over a period of 30 minutes, at which time a permanent blue color was obtained. TLC in cyclohexane-ethyl acetate (4:1) indicated that the starting material was no longer present and several new more polar products (R$_f$ 0.55, 0.5, 0.47, 0.4) had been formed. The reaction mixture was treated with 6.6 g (174 mmoles) of NaBH$_4$ and the cooling bath was removed. Stirring was continued for 1.5 hours and TLC showed the formation of a more polar (R$_f$ 0.2) product. The reaction mixture was acidified by the continuous dropwise addition of 200 ml of 2N HCl. The mixture was concentrated to remove the CH$_2$Cl$_2$ and the aqueous layer was extracted with three 100 ml portions of EtOAc which was washed with 50 ml of water, 100 ml of saturated NaHCO$_3$ and 50 ml of saturated NaCl. The EtOAc layer was dried (MgSO$_4$), filtered and concentrated to give 11.3 g of crude product which was chromatographed on 600 ml of silica gel; first eluting with 2400 ml of cyclohexane-ethyl acetate (5:2) and finally with 1600 ml of 2:1 cyclohexane ethyl acetate. Fractions containing only product were combined and concentrated to give 4 g (36%) of the desired compound.

NMR (CDCl$_3$) δ: 8.00–8.10 (m, 10H), 4.32, 4.86 (q 2H, J=12.5 Hz), 4.30, 4.42 (q, 2H, J=12 Hz), 3.61, 3.97 (ABX oct, 2H, $J_{AB}$ 12 Hz, $J_{AX}$ 5.5 Hz, $J_{BX}$=9 Hz), 2.35 (s, br, 1H), 1.46–1.62 (m, 1H), 1.02, 1.07 (dd, 1H, J=9 and 5.5 Hz), 0.70 (tr, 1H, J=5.5 Hz).

Step D:
1,1-Bis(benzoyloxymethyl)-2-toluenesulfonyloxymethylcyclopropane

A solution of 4.5 g (13.2 mmole) of 1,1-bis(benzoyloxymethyl)-2-hydroxymethylcyclopropane in 50 ml of dry pyridine was treated with 7 g (37 mmoles) of p-tosyl chloride and stirred at 22° for 1.5 hours. TLC in cyclohexane-ethyl acetate (2:1) (R$_f$ 0.6) indicated that the reaction was complete. The reaction was concentrated and the residue was dissolved in 150 ml of EtOAc and washed with 50 ml of water, 100 ml saturated NaHCO$_3$, four 250 ml portions of water and 50 ml of saturated NaCl. The ethyl acetate layer was dried (MgSO$_4$), filtered and concentrated to 9 g of residual solid. The crude product was chromatographed on 500 ml of silica gel in cyclohexane-ethyl acetate (5:1). Fractions containing only product were combined and concentrated to give 3.36 g (54%) of the title compound.

NMR (CDCl$_3$) δ: 7.22–8.06 (m, 14H), 4.18, 4.68 (q, 2H, J=12 Hz), 4.06, 4.38 (ABX oct, 2H, $J_{AB}$=11 Hz, $J_{AX}$=7 Hz, $J_{BX}$=9 Hz), 8.29 (s, 1H), 2.41 (s, 1H), 1.46–1.62 (m, 1H), 1.07, 1.12 (dd, 1H, J=9 Hz and 5.5 Hz), 0.76 (tr, 1H, J=5.5 Hz).

Step E:
2-Amino-9-[2,2-bis(benzoyloxymethyl)cyclopropylmethyl]-6-chloropurine A solution of 3.36 g (6.8 mmoles) of 1,1-bis(benzoyloxymethyl)-2-p-toluenesulfonyloxymethylcyclopropane in 15 ml of dry DMF (dimethylformamide) was added to a mixture of 1.37 g (8.2 mmoles) of 2-amino-6-chloropurine and 1.2 g (8.8 mmoles) of $K_2CO_3$ in 20 ml of DMF. The mixture was heated to 60° and stirred for 4 hours. The reaction was monitored by TLC in chloroform-methanol-water (95:5:0.3) $R_f$ 0.15, 0.9 (starting material), 0.4, 0.6 (Product). The reaction mixture was concentrated and the residue dissolved in 60 ml of $CHCl_3$—MeOH (1:1). About 20 ml of silica gel was added and the mixture was concentrated to dryness. The residue was added to the top of a 200 ml silica gel column and chromatographed in CMW (chloroform-methanol-water) (97.5:2.5:0.15). Fractions containing the two products (the 9 and 7 isomers) were cooled separately and concentrated to give 1.79 g (53%) of the title compound and 170 mg (5.1%) of the 7-isomer.

$\lambda_{max}$ (title compound) (MeOH): 308 nm ($\epsilon$=7,500).

NMR ($CDCl_3$) δ: 7.92 (s, 1H), 7.32–7.90 (m, 10H), 5.02 (s, br, 2H), 4.15–4.92 (m, 6H), 1.76–1.92 (m, 1H), 1.17, 1.22 (dd, 1H, J=5.8 Hz), 0.93 (tr, 1H, J=5.8 Hz).

Step F:
9-[2,2-Bis(hydroxymethyl)cyclopropylmethyl]quanine

A suspension of 1.78 g (3.62 mmoles) of 2-amino-9-[2,2-bis(benzoyloxymethyl)-1-cyclopropylmethyl]-6-chloropurine in 178 ml of 2.5N HCl was stirred at 100° for 4.5 hours; complete solution being obtained after one hour. TLC in CMW (70:30:3) showed that the reaction was almost complete. The reaction mixture was concentrated to a residual semi-solid which was triturated with three 20 ml portions of $Et_2O$ and dried. The residue was dissolved in 5 ml of water and neutralized (pH 7) with 2N NaOH. The solid which separated was removed and dried (600 mg) and the filtrate was concentrated to dryness (400 mg). The solids were combined, dissolved in a small amount of $CHCl_3$—MeOH (1:1) and put on five 2000 micron preparative TLC plates which were developed in CMW (70:30:3). The product bands ($R_f$ 0.3) were eluted with $CHCl_3$—MeOH (3:2) and when concentrated yielded 430 mg which showed a small impurity ($R_f$ 0.5). A 260 mg sample was dissolved in warm MeOH and 2 ml of Biorad AG-X2 (OH$^-$) 200–400 mesh resin was added. After stirring for 5 minutes the resin was filtered off and washed with MeOH. The resin was warmed with 45 ml of chloroform-methanolacetic acid (4:4:1) and filtered and washed. The filtrate was concentrated and gave 123 mg (13%) of the title compound. A sample recrystallized for analysis had m.p. 249°–250° d. λmax (pH 7, 0.1M phosphate buffer):254 nm ($\epsilon$=11,700), λshoulder 270 nm ($\epsilon$=8,800).

NMR (DMSO-$d_6$(dimethylsulfoxide)) δ:7.80 (s, 1H), 6.72 (s, br, 2H), 4.71 (tr, 1H, J=5.2 Hz), 4.61 (tr, 1H, J=5.5 Hz), 3.89, 4.11 (ABX oct, 2H, $J_{AB}$=14.5 Hz, $J_{AX}$=7.0 Hz, $J_{BX}$=8.5 Hz), 3.39, 3.77 (ABX Oct, 2H, $J_{AB}$=11.5 Hz, $J_{AX}$4.5 Hz, $J_{BX}$=6.0 Hz), 3.19, 3.46 (ABX oct, 2H, JAB 12.0 Hz, $J_{AX}$=6.0 Hz, $J_{BX}$=5.5 Hz), 1.18 (tr, br, 1H, J=4.0 Hz), 0.56, 0.60 (dd, 1H, J=4.0, 2.2 Hz), 0.46 (tr, 1H, J=2.2 Hz).

Analysis Calculated for $C_{11}H_{15}N_5O_3.0.5H_2O$: C, 48.17; H, 5.88; N, 25.54. Found: C, 48.00; H, 5.70; N, 25.28.

EXAMPLE 3
9-[2,2-Bis(hydroxymethyl)cyclopropylmethyl]adenine

Step A:
9-[2,2-Bis(benzoyloxymethyl)cyclopropylmethyl]-adenine

A suspension of 965 mg (7.14 mmoles) of adenine in 25 ml of dry DMF was stirred and 171 mg (7.14 mmoles; 286 mg of 60%) NaH emulsion was added. All of the NaH had reacted after 30 minutes and a solution of 3 g (6.5 mmoles) of 1,1-bis(benzoyloxymethyl)-2-(p-toluenesulfonyloxymethyl)cyclopropane (Example 2, product of Step D) in 10 ml of DMF was added and the mixture was heated at 40°. TLC in CMW (90:10:1), $R_f$ 0.2, 0.95 (starting materials) 0.45, 0.55 (products) showed that the reaction was complete in 3 hours. The mixture was concentrated to dryness and the residue was triturated with three 20 ml portions of ether, filtered and dried. The resultant solid was washed with twenty 3 ml portions of water and dried (1.2 g, largely a mixture of the two isomeric products). One gram of the crude product was chromatographed on five 2000 micron silica gel plates in CMW (95:3:0.3) and the zones (UV absorbing) at $R_f$0.29 and 0.18 (the 9 and 7 isomers, respectively) were eluted with CMW (70:30:3). After concentration of the solvents, there was obtained 670 mg (25%) of the title compound and 78 mg (2.5%) of the 7-isomer.

λmax (title compound) (MeOH): 260 nm ($\epsilon$=16,000).

NMR ($CDCl_3$) δ: 8.32 (s, 1H), 7.96 (s, 1H), 7.35–7.93 (m, 10H), 5.79 (s, br, 2H), 4.40, 4.92 (q, 2H, J=12.5 Hz), 4.33, 4.41 (q, 2H, J=12.5), 4.40 (d, 2H, J=9 Hz)) 1.82–1.93 (m, br, 1H), 1.16–1.21 (dd, 1H, J=6 Hz), 0.96 (tr, 1H, J=6 Hz).

Step B:
9-[2,2-Bis(hydroxymethyl)cyclopropylmethyl]adenine

A solution of 330 mg (0.71 mmoles) of 9-[2,2-bis(benzoyloxymethyl)cyclopropylmethyl]adenine in 15 ml of warm MeOH was stirred and about 10 mg of Na was added. The reaction was followed by TLC in CMW (80:20:2) ($R_f$ 0.4 (product); 0.7 (monobenzoates); 0.8 (starting material)) and the reaction was complete in 1 hour. The solution was concentrated and the residue was washed with three 15 ml portions of ether and dried. The solid was dissolved in water and the pH adjusted to 7 with dilute HCl. The solution was concentrated and the residue (240 mg) was chromatographed on three 1000 micron silica gel plates in CMW (80:20:2) and the product zone ($R_f$ 0.3) was eluted with CMW (70:30:3). Concentration gave a crystalline solid (120 mg; 68%).

Recrystallization from 1 ml of MeOH gave 100 mg of pure product m.p. 159°–160°. λmax (0.1M, pH 7 phosphate buffer) 261 nm ($\epsilon$=13,000).

NMR (DMSO-$d_6$) δ: 8.28 (s, 1H), 8.18 (s, 1H), 7.24 (s, br, 2H), 4.80 (tr, 1H, J=5.2 Hz), 4.58 (tr, 1H, J=5.6 Hz), 4.18, 4.33 (ABX oct, 2H, $J_{AB}$=14 Hz, $J_{AX}$=7.0 Hz, $J_{BX}$=8.0 Hz), 3.51, 3.85 (ABX oct, 2H, $J_{AB}$=12 Hz, $J_{AX}$=5.0 Hz, $J_{BX}$=7.0 Hz), 3.25, 3.51 (ABX oct, 2H, $J_{AB}$=11 Hz, $J_{AX}$4.5 Hz, $J_{BX}$=5.5 Hz), 1.23–1.39 (m, 1H), 0.61, 0.66 (dd, 1H, J=9 and 4.8 Hz), 0.51 (tr, 1H, J=4.8 Hz).

Analysis Calculated for $C_{11}H_{15}N_5O_2$ 0.2 $H_2O$: C, 52.25; H, 6.14; N, 27.69. Found: C, 52.45; H, 6.16; N, 27.64.

EXAMPLE 4

9-[(Z)-2,3-Epoxy-4-hydroxybutyl]-2-amino-6-chloropurine

Step A: 4-Benzoyloxy-2,3-cis-epoxybutanol

A solution of 3.34 g (20 mmoles of cis-2-butene-1,4-diol monobenzoate in 60 ml of $CHCl_3$ was mixed with 3.45 g (20 mmoles; 4.3 g of 80%) m-chloroperbenzoic acid. The mixture was stirred and warmed to 40°. The reaction was monitored by TLC in cyclohexane-EtOAc (3:2) ($R_f$ 0.5 (starting material), 0.35 (product)) and was complete in 4 hours. The reaction mixture was diluted with 100 ml of $CHCl_3$ and washed with saturated $NaHCO_3$ to remove m-chlorobenzoic acid. It was washed with saturated NaCl, dried ($MgSO_4$), filtered and concentrated to yield a residue of 4.1 g (98%) of the title compound, an oil which solidified on standing.

NMR ($CDCl_3$) δ: 7.42–8.12 (m, 5H), 4.58, 4.36 (ABX oct, 2H, $J_{AB}$=12 Hz, $J_{AX}$=5.3 Hz, $J_{BX}$=5.3 Hz) 3.92 (d, 2H, J=5.5 Hz), 3.18–3.42 (m, 2H).

Step B: 4-Benzoyloxy-2,3-cis-epoxybutyl α-toluenesulfonate

A solution of 3.08 g (10 mmoles) of 4-benzoyloxy-2,3-cis-epoxybutanol in 30 ml of pyridine was cooled to 0° and treated with 4.7 g (25 mmoles) of alpha-toluenesulfonyl chloride and stirred. The cooling bath was removed and as the temperature rose the reaction became very dark. TLC in cyclohexane-ethyl acetate (2:1) ($R_f$ 0.3 (starting material); 0.6 (product)) indicated that the reaction was complete in 15 minutes. The reaction mixture was concentrated at 30° to remove most of the pyridine and the residue was dissolved in 100 ml of EtOAc. The EtOAc solution was washed with 25 ml of water, 50 ml of 2N HCl, 25 ml of saturated $NaHCO_3$, 25 ml of saturated NaCl and dried ($MgSO_4$), filtered and concentrated to 3.3 g of residual oil. The crude product was chromatographed on 250 ml of silica gel in cyclohexane-EtOAc (4:1). Fractions containing only product were combined and concentrated to yield 1.61 g (45%) of the title compound.

NMR ($CDCl_3$) δ: 7.32–8.08 (m, 10H), 4.28, 4.44 (ABX oct, 2H, $J_{AB}$=13.5 Hz, $J_{AX}$=4.8 Hz, $J_{BX}$=6.0 Hz), 4.14, 4.32 (ABX oct, 2H, $J_{AB}$=12.0 Hz, $J_{AX}$=4.5 Hz, $J_{BX}$=7.2 Hz), 3.39, 3.42 (2 tr, 2H, J=4.5 Hz, J'=4.3 Hz), 3.26, 3.30 (2 tr, 1H, J=4.5 Hz, J=4.2 Hz).

Step C: 2-Amino-9-(4-benzoyloxy-2,3-cis-epoxybutyl)-6-chloropurine

A suspension of 424 mg (2.5 mmoles) of 2-amino-6-chloropurine in 10 ml of dry DMF was stirred and cooled to 0°. The cooling bath was removed and 60 mg (2.5 mmoles; 100 mg of 60%) NaH oil emulsion was added. Complete solution occurred after 15 minutes and a solution of 830 mg (2.29 mmoles) of 4-benzoyloxy-2,3-cis-epoxybutyl α-toluenesulfonate in 5 ml of DMF and the mixture was heated at 45°. TLC in CMW (90:10:1), ($R_f$ 0.25, 0.95 (starting materials), 0.7 (products)) indicated the reaction was complete. The reaction was concentrated and the residue was washed four times with 4 ml of ether and centrifuged and dried (1.1 g). The solid was then washed four times with 4 ml of water and dried. The residue (595 mg) was essentially a mixture of the 9 and 7 isomers. Recrystallization from MeOH gave 338 mg (38%) of the title compound. λmax (MeOH): 310 nm (ε=8300). NMR (DMSO-$d_6$) δ: 8.18 (s, 1H), 7.56–8.06 (m, 10H), 7.02 (s, br, 2H), 4.83, 4.50 (ABX oct, 2H, $J_{AB}$=13 Hz, $J_{AX}$=3 Hz, $J_{BX}$=6.8 Hz), 4.50, 4.32 (ABX oct, 2H, $J_{AB}$=14.5 Hz, $J_{AX}$=5 Hz, $J_{BX}$=6.5 Hz), 3.48–3.62 (m, 2H).

Step D: 2-Amino-6-chloro-9-[Z-2,3-epoxy-4-hydroxybutyl)]purine

A suspension of 330 mg (0.92 mmole) of 2-amino-9-(4-benzoyloxy-2,3-cis-epoxybutyl)-6-chloropurine in 20 ml of MeOH was stirred at 22° and 10 mg of Na was added. TLC in CMW (90:10:1) after 1 hour indicated that the reaction was slow, therefore an additional 20 ml of MeOH and 10 mg of Na were added. After 2 hours almost complete solution was obtained but then the product began to precipitate. The absence of starting material on TLC after 6 hours indicated that the reaction was complete. The mixture was concentrated to 13 ml, cooled and centrifuged, and the precipitate was washed with three 2 ml portions of MeOH and dried. The yield of product (m.p. 188°–190°) was 165 mg (67%). λmax (0.1M phosphate buffer) 307 (ε=7740), 246 (ε=5500). NMR (DMSO-$d_6$), δ: 8.16 (s, 1H), 6.99 (s, 2H), 5.12 (t, 1H, J=5.5 Hz), 4.20, 4.40 (ABX oct, 2H, $J_{AB}$=15 Hz, $J_{AX}$=4.5 Hz, $J_{BX}$=7.0 Hz), 3.67 (after decoupling triplet at 5.12), 3.80 (after decoupling triplet at 5.12), (ABX oct, 2H, $J_{AB}$=12 Hz, $J_{AX}$=5.0 Hz, $J_{BX}$=6.0 Hz), 3.42 (m, 1H), 3.20 (m, 1H).

Analysis Calculated for $C_9H_{10}ClN_5O_2$: C, 42.28; H, 3.94; N, 27.39. Found: C, 42.26; H, 3.95; N, 27.15.

EXAMPLE 5

9-[(Z)-2,3-Epoxy-4-hydroxybutyl]adenine

Step A: 9-(4-Benzoyloxy-2,3-cis-epoxybutyl)adenine

A suspension of 720 mg (5.36 mmoles) of adenine in 30 ml of dry DMF was stirred and 129 mg (5.36 mmoles; 215 mg of 60%) NaH emulsion was added. After 1 hour, the NaH had reacted and the suspension was treated with a solution of 4-benzoyloxy-2,3-cis-epoxybutyl α-toluenesulfonate (1.61 g, 4.44 mmoles) in 5 ml of DMF. The mixture was heated at 45° for 5 hours at which time TLC in CMW (90:10:1), ($R_f$=0.9, 0.2 (starting material), 0.6, 0.45 (product)) indicated that the reaction was complete. The mixture was concentrated to a pasty residue which was washed by decantation with several 5-ml portions of ether. The residue was dried and then washed with three 5 ml portions of water. The pasty mass crystallized and was filtered and dried to give 940 mg of mixture of isomers, mostly the 9-isomer. The mixture was recrystallized from 60 ml of MeOH and gave 470 mg of the title compound. The filtrate was concentrated and chromatographed on three 2000 micron silica gel plates in CMW (95:5:0.3) to give an additional 190 mg (total 660 mg; 42%) of product, m.p. 173°–176°, λmax (MeOH) 261 nm (ε=18,300), 230 nm (ε=18,900) and 34 mg (2.1%) of the 7-isomer; λmax (MeOH):273 nm (ε=12,700), 237 nm (ε=19,700). NMR ($CDCl_3$) δ: 8.38 (s, 1H), 7.46–8.12 (m, 5H), 7.96 (s, 1H), 5.62 (s, br, 2H), 4.22, 4.78 (ABX oct, 2H, $J_{AB}$=15 Hz, $J_{AX}$=3.8 Hz, $J_{BX}$=7.4 Hz), 4.56, 4.70 (ABX oct, 2H, $J_{AB}$=12 Hz, $J_{AX}$=5.0 Hz, $J_{BX}$=6.3 Hz), 3.52 (m, 2H).

Step B: 9-[(Z)-2,3-Epoxy-4-hydroxybutyl]adenine

A suspension of 170 mg (0.52 mmole) of 9-(4-benzoyloxy-2,3-cis-epoxybutyl)adenine in 10 ml of MeOH was stirred and 10 mg of Na was added. Complete solution was obtained in 20 minutes and TLC in CMW (80:20:2) ($R_f$=0.75, 0.55 (product)) indicated that the reaction was complete in 1.5 hours. The solution was corcentrated and the residue was washed with several portions of ether and dried (150 mg). The solid was chromatographed on two 1000 micron silica gel plates in CMW (80:30:2) and the product was recovered with CMW (70:30:3) to give, after concentration, 95 mg (83%) of the title compound. Recrystallization, from 1 ml of hot water, for analysis gave 25 mg of product, m.p. 180°–210° d, $\lambda_{max}$ (0.1M, pH 7 phosphate buffer) 261 nm ($\epsilon$=12,200).

NMR (DMSO-$d_6$) δ; 7.80 (s, 1H), 7.79 (s, 1H), 6.92 (s, br, 2H), 4.80 (tr, 1H, J=5.5 Hz), 3.92, 4.09 (ABX oct, 2H, $J_{AB}$=15.0 Hz, $J_{AX}$=5.0 Hz, $J_{BX}$=7.0 Hz), 3.20-3.44 (m, 2H) [$D_2O$ spike-3.68, 3.80 (ABX oct, 2H, $J_{AB}$=12.5 Hz, $J_{AX}$=6.5, $J_{BX}$=6.0 Hz] 3.34–3.46 (m, 1H), 3.12–3.26 (m, 1H).

Analysis Calculated for $C_9H_{11}N_5O_2$: C, 48.86; H, 5.01; N, 31.66. Found: C, 48.98; H, 5.00; N, 30.43.

EXAMPLE 6

9-[(Z)-2-(Hydroxymethyl)cyclopropylmethyl]adenine

Step A: Diethyl (Z)-cyclopropane-1,2-dicarboxylate

This material was prepared by a method similar to the literature procedures of G. B. Payne, *J. Org. Chem.*, 32, 3351 (1967) (for the diethyl ester), L. L. McCoy, *J. Am. Chem. Soc.*, 80 6568 (1958) (for the monoethyl monomethyl diester) and W. von E. Doering and K. Sachdev, *J. Am. Chem. Soc.*, 96, 1168 (1974) (for the dimethyl ester). In a 3-necked flask equipped with addition funnel, thermometer, nitrogen bubbler, and mechanical stirrer, a suspension of 40.0 g (1 mole) of sodium hydride (60% dispersion in mineral oil) in 250 ml of dry toluene was stirred at room temperature as a mixture of 108.3 ml (100.1 g, 1 mole) of ethyl acrylate and 84.5 ml (122.5 g, 1 mole) of ethyl chloroacetate was added dropwise. Even after addition of 0.5 ml of t-butanol, the reaction was not initiated until the temperature was raised to about 85° (oil bath). Within a few minutes at this temperature, the reaction became self-sustaining and the oil bath was removed. Hydrogen evolution continued as the temperature dropped, but after a few minutes an exotherm occurred (caution: vigorous foaming) and the reaction flask was immediately immersed in an ice bath. Cooling was continued until the mixture reached room temperature. The mixture was then added to cold $H_2O$ and extracted with ethyl acetate. The organic phase was dried with $MgSO_4$, filtered, and concentrated to give 220 g of amber residual oil. Fractional distillation afforded a total of 88.8 g of product, b.p. 98°–100° (4.5 mm); 90°–95° (2.5 mm), which was mainly cis-isomer, after collection of a small amount of the lower boiling trans-isomer. This was in agreement with the literature bp (83°–84° (1 mm): G. B. Payne, ref. cited above). The material was further purified by preparative high performance liquid chromatography (HPLC) through 2 Waters Prep Pak-500/silica columns (5 runs, elution with 93:7 hexane-ethyl acetate), giving 51.3 g (28%) of the cis-diester. Structure and purity were confirmed by 200 MHz NMR ($CDCl_3$) and analytical HPLC.

B. (Z)-1,2-Cyclopropanedimethanol

A 3-necked flask equipped with addition funnel, condenser, and nitrogen bubbler and containing 6.38 g (165 mmole) of lithium aluminum hydride was cooled in an ice bath as 160 ml of dry tetrahydrofuran was added. The ice bath was removed, and the mixture was stirred at ambient temperature as a solution of 20.5 g (110 mmole) of diethyl (Z)-1,2-cyclopropanedicarboxylate in 40 ml of tetrahydrofuran was added dropwise over 1.5 hours. The mixture was stirred at reflux for 2 hours and then overnight at room temperature. After cooling in an ice-methanol bath, the mixture was treated continuously with 37 ml of saturated aqueous ammonium chloride (added dropwise) and then with 40 ml of ethyl acetate. The insoluble salts were removed by filtration. The filtrate was concentrated, and the residue was taken up in ethyl acetate, dried with magnesium sulfate, filtered, and concentrated to give 6.32 g of oil. The salts which had been filtered off from the reaction mixture were re-suspended in a mixture of ethyl acetate and $H_2O$, neutralized with acetic acid, and stirred overnight at room temperature. The mixture was filtered, and the filtrate was extracted with more ethyl acetate. Tne organic solution was dried (magnesium sulfate), filtered, and concentrated to give an additional 2.56 g of product, for a total yield of 8.88 g (79%) of colorless oil. The 200 MHz NMR ($CDCl_3$) was in accord with the chemical shift values previously reported for this compound when obtained as a by-product from the diborane reduction of monomethyl cis-1,2-cyclopropanedicarboxylate [C. C. Shroff, W. S. Stewart, S. J. Uhm, and J. W. Wheeler, *J. Org. Chem.*, 36 3356 (1971)]. The compound has also been prepared by lithium aluminum hydride reduction of cis-1,2-cyclopropanedicarboxylic anhydride [E. Vogel, K. H. Ott, and K. Gajek, *Liebigs Ann. Chem.*, 644, 172 (1961)].

C. (Z)-2-(Benzoyloxymethyl)cyclopropanemethanol)

A mixture of 8.86 g (85 mmole) of (Z)-1,2-cyclopropanedimethanol, 10.3 ml (10.1 g, 128 mmole) of pyridine, and 90 ml of methylene chloride was stirred at 0° under nitrogen as 9.87 ml (11.95 g, 85 mmole) of benzoyl chloride was added dropwise. Stirring was continued at room temperature for 3 days. The mixture was then added to ice-water and extracted with ethyl acetate. The organic layer was backwashed twice with $H_2O$, dried with magnesium sulfate, filtered, and concentrated. The residual oil was chromatographed on a column of silica gel initially packed in hexane. Dibenzoate was eluted with 9:1 hexane-ethyl acetate, and subsequent elution with 3:1 hexane-ethyl acetare gave 5.6 g (32%) of the monobenzoyl ester. Structure and purity were confirmed by NMR ($CDCl_3$) and TLC (2:1 hexane-ethyl acetate).

D. (Z)-1-(Benzoyloxymethyl)-2-(chloromethyl)cyclopropane

A solution of 0.99 ml (1.61 g, 13.6 mmole) of thionyl chloride in 6 ml of chloroform was added dropwise to a mixture of 2.8 g (13.6 mmole) of cis-2-(benzoyloxymethyl)cyclopropanemethanol, 1.07 g (13.6 mmole) of pyridine, and 5 ml of chloroform that was stirred at 0° under nitrogen. The mixture was then heated at reflux for 1 hour under nitrogen. After concentration, the residual semi-solid was taken up in a mixture of diethyl ether and ethyl acetate and then filtered. Concentration of the filtrate gave 2.98 g (98%) of colorless oil which was suitable for use without further purification. Structure and purity were confirmed by NMR (CDCl$_3$).

E.
9-[(Z)-2-(Benzoyloxymethyl)cyclopropylmethyl]adenine

To a stirred suspension of 1.01 g (7.5 mmole) of adenine in 10 ml of dry dimethylformamide was added 0.33 g (8.3 mmole) of sodium hydride (60% in mineral oil). Owing to the insolubility of the resulting adenine sodium salt, the mixture was diluted with 7 ml of dry dimethyl sulfoxide, stirred mechanically under nitrogen, and heated at 80° as a solution of (Z)-1-(benzoyloxymethyl)-2-(chloromethyl) cyclopropane in 1 ml of dimethyl sulfoxide was added dropwise, followed by 112 mg (0.75 mmole) of sodium iodide. After 10 hours at 80°, an additional 1.01 g (6.75 mmole) of sodium iodide was added, and the temperature was raised to 100° and kept there overnight. The cooled mixture was concentrated under high vacuum to give a dark brown residue, which was taken up in methylene chloride and filtered. This solution was chromatographed on twenty-four 1000-micron preparative silica gel plates (developed with 80:20:2 chloroform methanol-water). The uv absorbing product band (R$_f$ about 0.7) was scraped from each plate, and the product was extracted from the silica gel with dimethylformamide. The extracts were concentrated under high vacuum. The residual oil was taken up in hot acetone, filtered to remove a small amount of insoluble material, and concentrated to give 220 mg (9%) of an oil, which was confirmed as the desired product by 200 MHz NMR.

F.
9-[(Z)-2-(Hydroxymethyl)cyclopropylmethyl]adenine

A mixture of 123 mg (0.38 mmole) of 9-[(Z)-2-(benzyloxymethyl)cyclopropylmethyl]adenine, 1.0 ml of 40% methylamine (aqueous), and 0.5 ml of methanol was stirred at room temperature overnight and at reflux for a total of 2 hours. After concentration, the residual oil was stirred with methylene chloride to give a solid which was collected on a filter. Recrystallization from isopropanol yielded 18 mg (20%) of white solid, m.p. 185.5–187.5. Stucture and purity were confirmed by 200 MHz NMR (DMSO-d$_6$) and TLC (80:20:2 chloroform-methanol-water).

Analysis Calculated for (C$_{10}$H$_{13}$N$_5$O 0.15 H$_2$O): C, 54.12; H, 6.04; N, 31.55. Found: C, 54.42; H, 5.95; N, 31.35.

EXAMPLE 7
1-[(Z)-2-(Hydroxymethyl)cyclopropylmethyl]thymine

A.
1-[(Z)-2-(Benzoyloxymethyl)cyclopropylmethyl]-thymine

A mixture of 1.26 g (10 mmole) of thymine, 2.47 g (11 mmole) of (Z)-1-(benzoyloxymethyl)-2-(chloromethyl)-cyclopropane, 2.76 g (20 mmole) of anhydrous potassium carbonate, 1.50 g (10 mmole) of sodium iodide, and 15 ml of dimethyl sulfoxide was stirred under nitrogen at 80°–90° overnight. After removal of salts by filtration, the filtrate was concentrated under high vacuum. The residual oil was chromatographed on a column of silica gel initially packed in hexane. Elution with 1:1 hexane-ethyl acetate removed some dialkylated product, while elution with ethyl acetate provided 1.26 g (40%) of white solid. The 200 MHz NMR (DMSO-d$_6$) was in accord with the assigned structure. A small sample recrystallized from isopropanol had mp 153°–155°.

B.
1-[(Z)-2-(Hydroxymethyl)cyclopropylmethyl]thymine

A mixture of 927 mg (2.95 mmole) of 1-[(Z)-2-(benzoyloxymethyl)cyclopropylmethyl]thymine, 8 ml of 40% methylamine (aqueous) and 4 ml of methanol was stirred at reflux for 2 hours and then at room temperature overnight. The solution was then concentrated under high vacuum. Trituration of the residual oil gave a white solid, which was isolated by filtration. Following similar collection of a smaller second crop, the total yield was 319 mg (51%), mp 168°–169°. Structure and purity were confirmed by TLC (90:10:1 chloroform-methanol-water) and 200 MHz NMR (DMSO-d$_6$).

Analysis: Calculated for C$_{10}$H$_{14}$N$_2$O$_3$.0.1 H$_2$O: C, 56.65; H, 6.75; N, 13.21. Found: C, 56.64; H, 6.72; N, 13.08.

EXAMPLE 8
1-[(Z)-2-(Hydroxymethyl)cyclopropylemthyl]cytosine

Step A:
1-[(Z)-2-(Benzoyloxymethyl)cyclopropylmethyl]cytosine

A mixture of 1.22 g (11 mole) of cytosine, 2.72 g (12 mmole) of (Z)-1-(benzoyloxymethyl)-2-(chloromethyl)-cyclopropane, 1.52 g (11 mmole) of anhydrous potassium carbonate, 1.65 g (11 mole) of sodium iodide, and 15 ml of dimethyl sulfoxide was stirred under nitrogen at 70° for 3 days. The mixture was filtered to remove insoluble salts and then concentrated under high vacuum. The viscous residual oil was partitioned between ethyl acetate and water. The organic layer was dried with magnesium sulfate, filtered, and concentrated. The residual oil was chromatographed on a column of silica gel (elution with ethyl acetate). Fractions containing clean product by TLC were combined and concentrated to give 178 mg of glassy residue. Structure and purity were confirmed by TLC (90:10:1 CHCl$_3$—MeOH—H$_2$O) and 200 MHz NMR (DMSO—d$_6$).

Step B:
1-[(Z)-2-(Hydroxymethyl)cyclopropylmethyl]-cytosine

A solution of 170 mg (0.57 mmole) of 1-[(Z)-2-(benzoyloxymethyl)cyclopropylmethyl]cytosine in 2 ml of methanol was treated with 3–4 drops of 1M methanolic sodium methoxide and then stirred at room temperature under protection from moisture for 1 day. Concentration to dryness gave a glassy residue. Trituration with isopropanol at 0° gave a white solid, which was collected by filtration. This material was dissolved in boiling ethyl acetate and filtered to remove a small amount of insoluble solid. Concentration of the filtrate followed by vacuum drying yielded 12 mg of white solid, m.p. 145°–146.5°. The product was homogeneous by TLC (ethyl acetate), and the structure was confirmed by 200 MHz NMR (DMSO-d$_6$).

Analysis for C$_9$H$_{13}$N$_3$O$_2$.0.1 H$_2$O: Calculated: C, 54.84; H, 6.75; N, 21.33. Found: C, 55.17; H, 6.68; N, 21.09.

EXAMPLE 9

9-[(Z)-2-(Hydroxymethyl)cyclopropylmethyl]-7-deazaguanine

Step A:
6-[(Z)-2-(Hydroxymethyl)cyclopropylmethylamino]isocytosine

Based on the general method of C. W. Noell and R. K. Robins, *J. Med. Pharm. Chem.*, 5, 558 (1962), stir a mixture of 5 mmole of 6-isocytosine, 15 mmole of (Z)-2-(hydroxymethyl)cyclopropylmethylamine, and 2.5 ml of 2-ethoxyethanol at reflux under nitrogen until TLC shows complete reaction (1 to 2 hours). Concentrate the solution under high vacuum, and isolate the product by column chromatography on silica gel.

Step B:
9-[(Z)-2-(Hydroxymethyl)cyclopropylmethyl]-7-deazaguanine

Using the general method of C. W. Noell and R. K. Robins, *J. Heterocycl. Chem.*, 1, 34 (1964), stir a mixture of 1 mmole of 6-[(Z)-2-(hydroxymethyl)cyclopropylmethylamino]isocytosine, 1.22 mmole of sodium acetate, and 2 ml of water in an oil bath at about 70° and treat with 1.05 mmole of 45°-55% chloroacetealdehyde (aqueous). After stirring at this temperature for 5 minutes, cool the mixture. Collect the solid on a filter, wash with cold water, and purify by recrystallization.

EXAMPLE 10

9-[(Z)-2-(Hydroxymethyl)cyclopropylmethyl]-7-deazaguanine (Alternate Method)

Step A:
2-Amino-7-[(Z)-2-(benzoyloxymethyl)cyclopropylmethyl]-4-methoxy-7H-pyrrolo[2,3-d]pyrimidine To a stirred suspension of 10.5 mmole of sodium hydride in 10 ml of dry N,N-dimethylformamide maintained under a nitrogen blanket add 10 mmole of 2-amino-4-methoxy-7H-pyrrolo[2,3-d]-pyrimidine [prepared as described by F. Seela, A. Kehne, and H. D. Winkeler, *Liebigs Ann. Chem.*, 137 (1983)]. Continue stirring under nitrogen near room temperature, cooling in an ice bath as necessary to control the exotherm. When hydrogen evolution has ceased add 10 mmole of (Z)-1-(benzoyloxymethyl)-2-(chloromethyl)cyclopropane and 10 mmole of sodium iodide and stir the resulting mixture under nitrogen at about 50°-80° overnight. Filter the mixture and concentrate the filtrate to dryness under high vacuum. Isolate the product by column chromatography on silica gel.

Step B:
2-Amino-7-[(Z)-2-(hydroxymethyl)cyclopropylmethyl]-4-methoxy-7H-pyrrolo[2,3-d]pyrimidine Treat a stirred solution of 2-amino-7-[(Z)-2-(benzoyloxymethyl)cyclopropylmethyl]-4-methoxy-7H-pyrrolo[2,3-d]pyrimidine in methanol with a catalytic amount of methanolic sodium methoxide. Maintain the reaction at room temperature or warm if desired until TLC indicates complete conversion to the more polar product. After neutralization with glacial acetic acid, concentrate the solution to dryness and purify the product by recrystallization.

Step C:
9-[(Z)-2-(Hydroxymethyl)cyclopropylmethyl]-7-deazaguanine, also named 2-amino-3,7-dihydro-7-[(Z)-2-(hydroxymethyl)cyclopropylmethyl]-4H-pyrrolo-[2,3-d]pyrimidin-4-one Removal of the O-methyl protecting group may be accomplished by the method of Seela [F. Seela, A. Kehne, and H. D. Winkeler, *Liebigs Ann. Chem.*, 137 (1983); H. D. Winkeler and F. Seela, *J. Org. Chem.*, 48, 3119 (1983)]. Thus, treat a suspension of 1 mmole of 2-amino-7-[(Z)-2-(hydroxymethyl)cyclopropylmethyl]-4-methoxy-7H-pyrrolo[2,3-d]pyrimidine in 10 ml of dry toluene with 1.5 mmole of sodium p-thiocresolate and 1.5 mmole of dry hexamethylphosphoric triamide. Stir the mixture at reflux under nitrogen for about 3 hours and then concentrate it. Isolate the product from the residue by chromatography on silica gel.

EXAMPLE 11

1-[(Z)-2-(Hydroxymethyl)cyclopropylmethyl]-6-azauracil

Step A:
1-[(Z)-2-(Benzoyloxymethyl)cyclopropylmethyl]-6-azauracil

Stir a mixture of 10 mmole of 6-azauracil, 11 mmole of (Z)-1-(benzoyloxymethyl)-2-(chloromethyl) cyclopropane, 20 mmole of anhydrous potassium carbonate, 10 mmole of sodium iodide, and 15 ml of dimethyl sulfoxide under nitrogen at about 60°-90° overnight. Filter the mixture and concentrate the filtrate under high vacuum. Isolate the product from the residue by chromatography on silica gel.

Step B:
1-[(Z)-2-(Hydroxymethyl)cyclopropylmethyl]-6-azauracil

Stir a mixture of 3 mmole of 1-[(Z)-2-(benzoyloxymethyl)cyclopropylmethyl]-6-azauracil, 8 ml of 40% methylamine (aqueous), and 4 ml of methanol at reflux for about 2 hours. The mixture may be allowed to stir at room temperature overnight. Then, concentrate the solution. Crystallize the residue to obtain the desired product.

EXAMPLE 12

Synthesis of 9-[(Z)-2-(Hydroxymethyl)cyclopropylmethyl]-8-azaguanine

Shake a mixture of 5 mmole of 6-[(Z)-2-(hydroxymethyl)cyclopropylmethylamino]-5-nitrosoisocytosine, 200 mg of 10% palladium on carbon, and 65 ml of glacial acetic acetic with hydrogen (initial pressure approximately 3 atmospheres) in a Parr apparatus. After TLC shows complete reduction (appoximtely 30 minutes), remove the catalyst by filtration under nitrogen. Add to the filtrate a solution of 5 mmole of sodium nitrite in 25 ml of water. Stir the resulting solution under nitrogen at room temperature for 30 minutes and then concentrate under high vacuum. Triturate the residue with cold water to obtain the product, which should be purified by recrystallization.

EXAMPLE 13

9-[(Z)-2-(Hydroxymethyl)cyclopropylmethyl]-3-deazaguanine

Step A: Methyl 1-[(Z)-2-(Benzoyloxymethyl)cyclopropylmethyl]-5-cyanomethyl-imidazole-4-carboxylate The starting imidazole may be converted to its silyl derivative using the procedure of P. D. Cook, R. J. Rousseau, A. M. Mian, P. Dea, R. B. Meyer, Jr., and R. K. Robins, *J. Am. Chem. Soc.*, 98, 1492 (1976). Thus stir a mixture of 75 mmole of methyl 5-cyanomethylimidazole-4-carboxylate (P. D. Cook, et al., cited above), 150 ml of hexamethyldisilazane, and 250 mg of ammonium sulfate at reflux under nitrogen for 12 hours. Concentrate the cooled solution in vacuo to give the trimethylsilyl derivative as an oil. Dissolve this material in about 200 ml of dry xylene and treat with 75 mmole of (Z)-1-(benzoyloxymethyl)-2-(chloromethyl)cyclopropane. Stir the resulting solution at reflux under an inert atmosphere until TLC shows optimized product formation, e.g. 24 hours. Concentrate the mixture to dryness and isolate the product from the residue by chromatography on silica gel.

Step B: 5-Cyanomethyl-1-[(Z)-2-(hydroxymethyl)cyclopropylmethyl]imidazole-4-carboxamide This reaction may be carried out using conditions based on those of P. D. Cook, et al. (cited above). Heat a mixture of 10 mmole of methyl 1-[(Z)-2-(benzoyloxymethyl)cyclopropylmethyl]-5-cyanomethylimidazole-4-carboxylate and 30 ml of liquid ammonia in a sealed vessel at about 60° for 2 days (or, optionally, at 90°–100° for 3–7 hours). After evaporation of the ammonia, isolate the product from the residue by chromatography on silica gel.

Step C: 9-[(Z)-2-(Hydroxymethyl)cyclopropylmethyl]-3-deazaguanine

Again, the synthesis is based on the reaction conditions described by P. D. Cook, et al. (cited above). Stir a mixture of 5 mmole of 5-cyanomethyl-1-[(Z)-2-(hydroxymethyl)cyclopropylmethyl]imidazole-4-carboxamide, 12.5 ml of 5% sodium carbonate solution and 8 ml of ethanol at reflux for about 1 hour. Neutralize the cooled mixture by gradual addition of acetic acid. Isolate the solid on a filter and wash with water to give the desired product.

EXAMPLE 14

| Oil in Water Cream Base | |
| --- | --- |
| 9-[(Z)-2-(Hydroxymethyl)cyclopropylmethyl]guanine | 5.0 g |
| Lanolin, Anhydrous | 20.0 g |
| Polysorbate 60 | 4.0 g |
| Sorbitan Monopalmitate | 2.0 g |
| Light Liquid Paraffin | 4.0 g |
| Propylene Glycol | 5.0 g |
| Methyl Hydroxybenzoate | 0.1 g |
| Purified Water to | 100.0 g |

EXAMPLE 15

| Water Soluble Ointment Base | |
| --- | --- |
| 9-[(Z)-2-(Hydroxymethyl)cyclopropylmethyl]guanine | 0.5 g |
| Glycerol | 15.0 g |
| Macrogol 300 | 20.0 g |
| Polyethylene Glycol 1500 | 64.5 g |

EXAMPLE 16

| Tablet - (Total weight 359 mg) | |
| --- | --- |
| 9-[(Z)-2-(Hydroxymethyl)cyclopropylmethyl]guanine | 100 mg |
| Lactose | 200 mg |
| Starch | 50 mg |
| Polyvinylpyrrolidone | 5 mg |
| Magnesium Stearate | 4 mg |

For each of Examples 14–16, combine the listed ingredients by standard techniques.

What is claimed is:

1. A compound of the formula

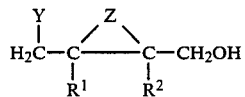

and the pharmaceutically acceptable salts thereof wherein Y is a purin-9-yl or a heterocyclic isostere of a purin-9-yl group; $R^1$ is selected from hydrogen and alkyl of 1 to 4 carbon atoms; $R^2$ is selected from hydrogen, alkyl of 1 to 4 carbon atoms, and —CH$_2$OH; and Z is >CH$_2$ or >O.

2. A compound according to claim 1 wherein Y is a purin-9-yl group.

3. A compound according to claim 1 wherein Y is

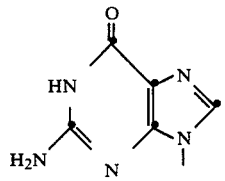

4. A compound according to claim 1 wherein Y is

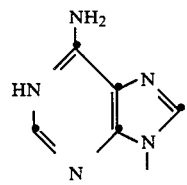

5. A compound according to claim 1 wherein Y is

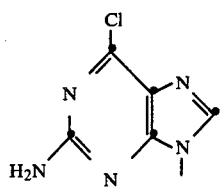

6. 9-[(Z)-2-(Hydroxymethyl)cyclopropylmethyl]guanine, according to claim 1.

7. An antiviral pharmaceutical composition comprising an effective amount of a compound of claim 1 and a pharmaceutically acceptable carrier.

8. A method of treating virus infections in mammals comprising administering to a mammal in need of such treatment an effective amount of a compound of claim 1.

* * * * *